United States Patent [19]

Hoffmann

[11] 4,208,203

[45] Jun. 17, 1980

[54] METHOD OF PROTECTING CORN FROM HERBICIDES

[75] Inventor: Otto L. Hoffmann, Shawnee Kans.

[73] Assignee: Gulf Research & Development Co., Pittsburgh, Pa.

[21] Appl. No.: 329,938

[22] Filed: Feb. 5, 1973

Related U.S. Application Data

[63] Continuation-in-part of Ser. No. 181,580, Sep. 17, 1971, Pat. No. 4,033,756.

[51] Int. Cl.$^2$ .............................................. A01N 9/22
[52] U.S. Cl. ........................................ 71/95; 71/100; 71/118
[58] Field of Search .............................. 71/77, 100, 95

[56] References Cited

U.S. PATENT DOCUMENTS

| | | | |
|---|---|---|---|
| 2,913,327 | 11/1959 | Hilles | 71/100 |
| 3,131,509 | 5/1964 | Hoffman | 71/77 X |
| 3,399,988 | 9/1968 | Soong et al. | 71/95 |
| 3,719,466 | 3/1973 | Ahle | 71/106 |
| 3,778,247 | 12/1973 | Pyne et al. | 71/95 |
| 3,794,683 | 2/1974 | Gassner et al. | 71/118 |
| 3,804,853 | 4/1974 | D'Amico et al. | 71/95 |
| 3,888,925 | 6/1975 | Phillips | 71/95 |
| 4,021,224 | 5/1977 | Pallos et al. | 71/100 |
| 4,033,756 | 7/1977 | Hoffmann | 71/100 |

OTHER PUBLICATIONS

Hamm et al., "Effect of Variations in the Acyl, etc.," (1957), J. Agr. & Food Chem., vol. 5, pp. 30-32 (1957).

Primary Examiner—Glennon H. Hollrah
Attorney, Agent, or Firm—Carl A. Cline

[57] ABSTRACT

Corn is protected from S-alkyl thiocarbamate herbicides, while obtaining good control of unwanted plant species by applying to the soil in the vicinity of corn seed an effective but non-phytotoxic amount of an N,N-diisopropyl, N-benzyl-N-methyl, N-benzyl-N-ethyl, N-(p-methoxybenzyl), N-methyl-N-phenethyl or N,N-diethyl amide of dichloroacetic, dibromoacetic or tribromoacetic acids.

1 Claim, No Drawings

METHOD OF PROTECTING CORN FROM HERBICIDES

DESCRIPTION OF THE INVENTION

This application is a continuation-in-part of U.S. patent application Ser. No. 181,580 filed Sept. 17, 1971, now U.S. Pat. No. 4,033,756, which is incorporated herein by reference.

Antagonism of a herbicide in the soil by another chemical, which may also be a herbicide, has been known for over three decades. (See, for instance, Crafts and Cleary, Hilgardia, 10 p. 401 (1936)). In general, most of the antagonistic effects observed have not been very great, particularly when both chemicals have been applied to the soil, or to growing plants or plant cuttings. The only commercial use of a herbicide antagonist has been in the treatment of corn seed to protect the young corn plants from large quantities of thiocarbamate herbicides employed to control particularly heavy weed infestations.

In the patent application referred to above it is disclosed that some members of a novel class of seed treating agents appear to migrate away from the corn seed over a period of time, some of them apparently then beginning to protect nearby seeds of weeds and volunteer crop seeds. Because extremely small quantities of chemicals are used to treat corn seed to protect them, this migration may result in a loss of protection of the corn and perhaps reduced weed control near the row of corn plants, where it is most needed.

Although direct treatment of corn seed with a protective agent is the most economical method with respect to the quantity of chemicals, it does require some extra labor at planting time. If the protective agent is not too expensive, it would be desirable to mix it with the thiocarbamate herbicide or with the fertilizer when it is applied to the soil in the corn row, so as to avoid extra hand labor and extra passes through the field. This is particularly true in ordinary corn farming in which the crop is not grown for seed and a few volunteer corn plants can be tolerated.

Seed protecting agents which can be applied to the soil must have some of the previously observed ability to diffuse through soil, so that enough compound will reach the corn seed to protect it from the herbicide. However, the agent must not diffuse away so rapidly that the concentration of seed protecting agent decreases faster than herbicide concentration. Furthermore, the protecting agent must not be a general antagonist for the herbicide, or it will also protect the weeds. I have discovered that a few compounds appear to have a sufficiently strong protective effect which is specifically limited to corn and also possess the other necessary properties, so they can be applied to the soil in the vicinity of the corn seed. They can be sprayed over the surface of the soil alone or along with the herbicide before planting, after dropping of the seed before covering, or after planting and will give protection to the corn without protecting other species.

According to this invention, corn is protected from S-alkyl thiocarbamate herbicides by the method which comprises applying to the soil in the vicinity of the corn seed an effective but non-phytotoxic amount of an N,N-diisopropyl, N-benzyl-N-methyl, N-benzyl-N-ethyl, N-(p-methoxybenzyl), N-methyl-N-phenethyl or N,N-diethyl amide of dichloroacetic, dibromoacetic or tribromoacetic acid. Most economical use of the chemical is probably achieved by band application along with liquid fertilizer, if this method of fertilization is employed. However, the present trend in corn culture is to plant the rows of corn so close together that band applications are becoming impractical. Since the protecting agent must be present in the vicinity of the corn seed at the same time as the herbicide, it is convenient to apply both substances in the same operation. The preferred agents are the N,N-diisopropyl amides. These compounds are economical to use and are effective over a broad range of application rates, without apparent undesirable side effects.

The method of manufacture of the soil-applied seed protecting agents, as well as the method of use are illustrated below:

SYNTHESIS OF PROTECTIVE AGENTS

Chemicals employed in the method of this invention may be made by reacting one molar equivalent of the acid chloride with two molar equivalents of the amine (one molar equivalent of diamines). For the preparation of small amounts in the laboratory, the reaction may be carried out in ether. After reacting the ether is evaporated and the chemicals may be used without further purification. In commercial manufacture, particularly for the purpose of reducing corrosion problems, the amine hydrochloride is preferably removed from the reaction mixture, but this step is not essential to demonstrate the beneficial effect of most of the chemicals. A description of the simple procedure for amide synthesis in ether solution is found in *Journal of the Indian Chemical Society*, vol. 25, pages 483-484 (1948).

An efficient procedure which yields purified amides is found in *Journal of Medicinal Chemistry*, vol. 9, pages 704-707 (1966). A procedure employed to prepare many of the amides is presented below by way of illustration.

PREPARATION OF N,N-DIISOPROPYLDICHLOROACETAMIDE

To a solution of diisopropylamine (6.8 g) (0.068 mol) and 6.8 g. of triethylamine in 100 ml of anhydrous benzene was added dropwise at 15° C. with stirring and ice-bath cooling, dichloroacetyl chloride (10.0 g, 0.068 mol). The solution was stirred overnight at room temperature. The benzene solution was washed successively with 10% HCl, $H_2O$ sodium hydroxide and saturated NaCl solution and was dried over anhydrous $MgSO_4$. The solvent was distilled off, yielding 4.9 g. of liquid product, which infrared absorption spectra indicated to be substantially pure. No further purification was considered to be necessary for the purpose of this invention.

CHEMICAL PROTECTION OF SEEDS FROM HERBICIDES

The chemicals listed above were employed as seed protectants at various concentrations as follows. Combinations of one pound and one-half pound per acre of the protective agent and 8 and 16 pounds per acre EPTC were applied to greenhouse flats seeded with rice, oats, rye, barley, cotton, wheat, corn, peas, soybeans, cabbage, grain sorghum, sugar beet, alfalfa, tomato and flax. The chemicals were applied in water directly over the seed. Seeds were then covered immediately with ½ inch soil and watered. Unprotected corn was also treated with EPTC for comparison purposes.

After two weeks the chemicals listed above protected the corn plants so that they were free of injury.

None of the other 14 crops was protected by any of the tested chemicals. In this experiment EPTC killed the unprotected corn.

In another, more severe test, EPTC was applied to the soil in the vicinity of corn seed at the rate of 16 lb/A and each of the protecting chemicals was applied to the soil at the same time at a rate of only one half pound per acre. At the end of four weeks, there was still complete protection of corn from injury by EPTC by all of the following seed protecting agents:

DICHLOROACETAMIDES

N,N-diisopropyldichloroacetamide
N-benzyl-N-methyldichloroacetamide
N-benzyl-N-ethyldichloroacetamide
N-methyl-N-phenethyldichloroacetamide
N-(p-methoxybenzyl)dichloroacetamide

DIBROMOACETAMIDES

N,N-diisopropyldibromoacetamide
1-dibromoacetyl-2,5-dimethylpyrrolidine

TRIBROMOACETAMIDES

N,N-diisopropyltribromoacetamide
N,N-diethyltribromoacetamide

EPTC was selected for use to demonstrate the protective effect because of its very high activity and potentially injurious effects. In general, protection of corn from this herbicide is more difficult than is true of the other commercial thiocarbamate herbicides.

I claim:

1. The method of protecting corn from injury by an S-alkyl thiocarbamate pre-emergent herbicide comprising applying to the soil in the vicinity of the corn seed an effective but non-phytotoxic amount of 1-dibromoacetyl-2,5-dimethylpyrrolidine.

* * * * *